United States Patent [19]
Langguth

[11] 3,958,564
[45] May 25, 1976

[54] EKG CONTACT

[75] Inventor: Arthur F. Langguth, San Diego, Calif.

[73] Assignee: The United States of America as represented by the Secretary of the Navy, Washington, D.C.

[22] Filed: May 9, 1975

[21] Appl. No.: 576,080

[52] U.S. Cl. ............... 128/2.06 E; 128/2.1 E; 128/DIG. 4
[51] Int. Cl.² .......................................... A61B 5/04
[58] Field of Search ....... 128/2.06 E, 2.1 E, DIG. 4, 128/404, 418, 2.05 E, 2.05 P, 2.05 S, 2 K; 248/206 R, 467, 362, 363

[56] References Cited
UNITED STATES PATENTS

| | | | |
|---|---|---|---|
| 1,487,998 | 3/1924 | Woolf | 128/418 |
| 2,045,672 | 6/1936 | Oliveri | 248/206 R |
| 2,580,628 | 1/1952 | Welsh | 128/2.06 E |
| 3,534,733 | 10/1970 | Phipps | 128/2.1 E |
| 3,568,663 | 3/1971 | Phipps | 128/2.06 E |
| 3,735,753 | 5/1973 | Pisarski | 128/2.1 E |

FOREIGN PATENTS OR APPLICATIONS

| | | | |
|---|---|---|---|
| 333,982 | 12/1958 | Switzerland | 128/418 |
| 508,421 | 1/1955 | Italy | 248/206 R |

*Primary Examiner*—William E. Kamm
*Attorney, Agent, or Firm*—Richard S. Sciascia; Ervin F. Johnston; Thomas Glenn Keough

[57] ABSTRACT

An improved electrical contact is configured to provide more accurate electrical potential readings. Electrocardiograms and electroencephlograms, for example, require that a monitoring electrode be firmly held on a creature's body to give valid readouts. To that end, a suction cup is cast integrally from a resilient compound to create a sufficient suction when it is pressed against a surface. An annular shoulder portion molded in the suction cup engages a projection from the electrode and holds the electrode firmly on the surface. The suction cup's relatively wide lip ensures the continued creation of the vacuum while the biasing force of the annular shoulder on the extension ensures responsive operation over a prolonged period of time.

3 Claims, 5 Drawing Figures

EKG CONTACT

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

Scientists and researchers, as well as physicians, from time to time rely upon monitoring the electrical potentials created during some physiological phenomena in animals or patients. Electrocardiograms, electroencephlograms, etc. are recognized as valuable aids and are frequently relied upon to facilitate a thorough diagnosis and the proper remedial treatment. But, the soundness of the diagnosis is dependent on the accuracy of the available information. A long standing problem is that of securing the electrodes firmly during the information gathering period. One solution, of course, is to surgically implant sensors; however, this is time consuming and generally is unacceptable for a variety of other reasons. Adhesive tape often is used and works under controlled conditions in the lab. Yet, when the test subject is perspiring heavily or if it is a marine mammal underwater, the wetness loosens the tape and the electrodes slip off. Thus, there is a continuing need in the state of the art for an electrode for sensing the internal electrical potentials in living animals which reliably is held in place for a prolonged period of time.

SUMMARY OF THE INVENTION

The present invention is directed to providing an apparatus located on the body of a living animal for sensing internal electrical potentials. An electrical contact has a resilient outwardly reaching member coupled to remote circuitry for performing an electrocardiogram, electroencephlogram, etc. A suction cup resiliently engages the outwardly reaching member and holds it firmly against the animal's body while a resilient lip portion sealably holds the suction cup and contact on the animal's body.

It is a prime object of the invention to provide and improved electrical contact.

Another object is to provide an improved suction cup capable of being applied single-handedly.

Yet another object is to provide a suction cup and electrical contact configured for mechanical cooperation to ensure long term monitoring of internal electrical potentials.

Yet another object is to provide an improved contact configured to reliably monitor internal electrical potentials from marine mammals.

Another object is to provide an improved electrical contact relying upon an integrally formed suction cup for holding an electrode on a surface.

Still a further object of the invention is to provide an improved electrical contact configured to allow one handed attachment on an animal's body.

These and other objects of the invention will become more readily apparent from the ensuing description when taken with the drawings.

DESCRIPTION OF THE PREFERRED EMBODIMENT

Figure 1:
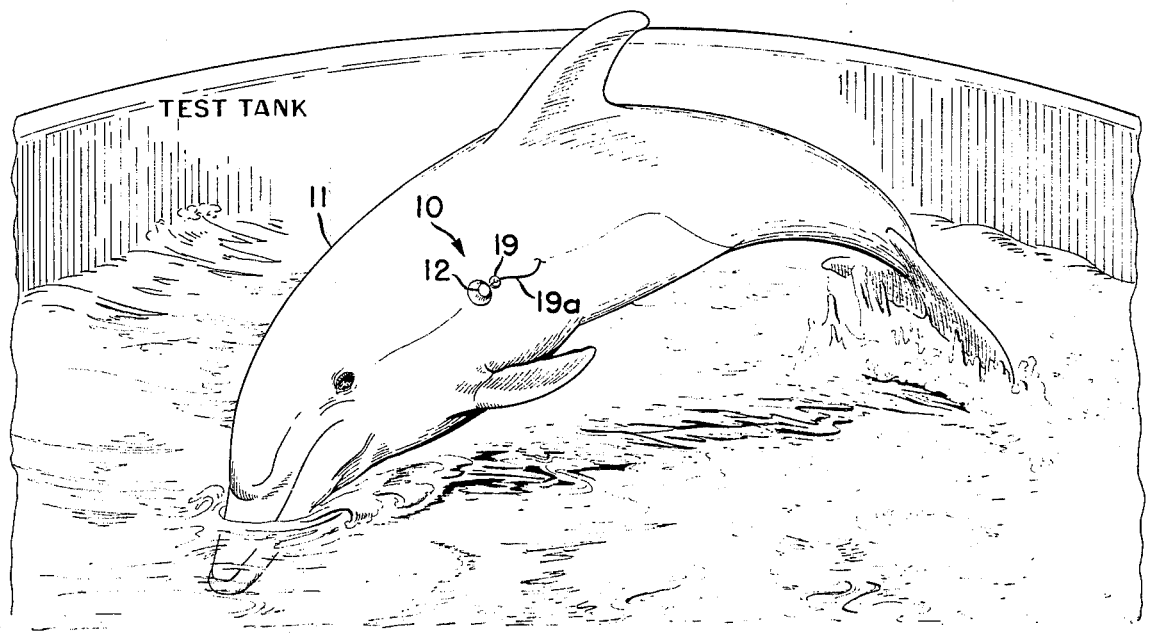
FIG. 1 is an isometric depiction of the invention suitably connected for an electrocardiogram on a dolphin.

Referring now to FIG. 1 of the drawings, a representative embodiment of the improved contact 10 is shown appropriately positioned on a lateral projection of the thoracic cavity of a dolphin 11. Such a location enables scientists and researchers to record an electrocardiogram of the animal as it swims in a test tank. While what is shown is the mounting of a contact on a swimming marine mammal, the device of the invention optionally is deployed in a wide variety of situations where some phenomena such as electrocardiograms or electroencephlograms provide representative electrical potentials of some physiological phenomena.

A major contributor to the high degree of reliability afforded by the instant invention is attributed to a uniquely configured suction cup 12. The suction cup is integrally molded from a resilient composition, such as rubber.

Figure 2:
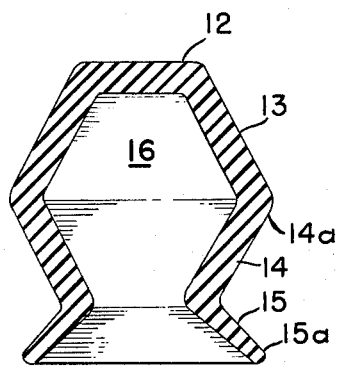
FIG. 2 is a cross-sectional representation of the suction cup in the extended position.
Figure 4:
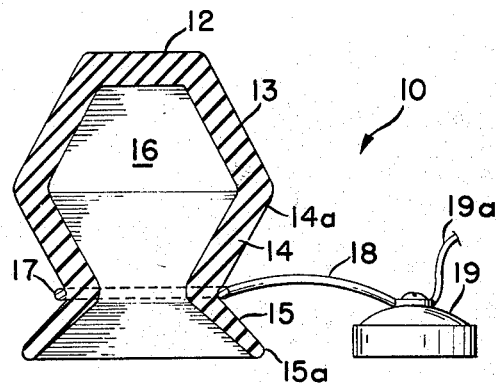
FIG. 4 is a depiction of an extended suction cup connected to an electrode.
Figure 5:
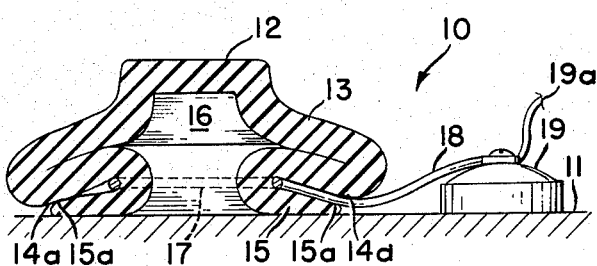
FIG. 5 shows the invention held on the body of an animal.

A representative resilient material from which the suction cup is cast is an E-series RTV mold making rubber marketed by the Dow Corning Company under the trade designation of "Silastic". Such a material possesses the resiliency to bias a suitably molded suction cup such as the device of this invention to its extended position as shown in FIGS. 2 and 4, particularly after the cup has been cured for one hour at a 212°F temperature.

The suction cup is made up of three portions. These are an essentially cup-shaped shell portion 13 extending into a frustoconically shaped shell portion 14, and a radially flaring lip portion 15. Thusly configured, when the suction cup is in a relaxed state, a relatively spacious chamber 16 is enclosed as the lips abut a surface or body of an animal, see FIG. 2.

Figure 3:
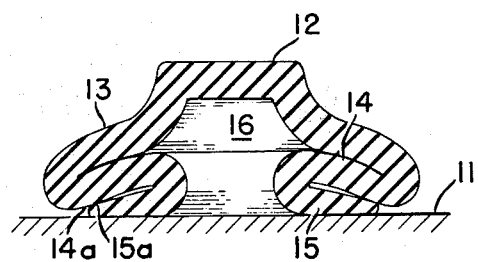
FIG. 3 shows the suction cup held in place on a surface.

FIG. 3 best depicts a suction cup in its compressed state. In this condition, the resilience of the lip portion accommodates the surface while the lip portion, frustoconical portion and cup-shaped portion together urge the suction cup to reassume its relaxed shape shown in FIG. 2. This urging or biasing of the portions creates a vacuum or suction on the surface and holds the cup on location.

The vacuum pulls shoulders 14a of frustoconical portion 14 down upon an exposed surface 15a of lip portion 15 to aid the lip in maintaining its sealed engagement on the surface. The chances for the lip's breaking away from the surface are thereby reduced and attachment to the surface for a prolonged period of time is assured.

The aforedescribed suction cup functionally cooperates with related structure to assure a long term electrical monitoring of a physiological phenomena. A ring-shaped element 17 is carried about the circumference of the line of juncture between the frustoconical portion and the lip portion. A spring-wire element 18 is secured to the ring-shaped element and at its outwardmost extension is joined to an electrode 19.

The electrode is any one of a variety of suitable constructions for sensing internal electrical potentials and may be in its simplest form no more than a metal, such as stainless steel. Irrespective what exact material is chosen, representative signals sensed by the electrode are passed to remotely located circuitry via a lead 19a.

This apparatus thusly described is capable of being affixed onto a surface by a simple one-handed operation. The suction cup depicted in FIG. 2 is grasped by placing the index and middle fingers on opposite diametric positions on the frustoconical shell 14. The thumb is placed on the axially exposed surface of cup-shaped shell portion 13 and depressed. When the cup is formed into the configuration shown in FIG. 3 it is pressed onto a surface by continuing pressure by the thumb. Releasing the thumb's pressure sticks the cup on the surface.

This invention is easily mounted on a surface such as the body of a marine mammal in the manner discussed above. The suction cup is compressed and surface 15a of lips 15 are placed on the attachment surface. Shoulders 14a of the frustoconical portion 14 bear down upon the outwardly reaching element 18. This force, in turn, is transmitted to the electrode 19, causing it to firmly bear upon the attachment surface. Being so biased and held in place, long term, reliable monitoring of a physiological phenomena is assured. Even in the case of a marine mammal swimming rapidly through the water in a test tank, a relatively reliable indication is provided. Of course, in such a free moving application, lead 19a is of a sufficient length or properly tethered to transmit the signals responsively without failure.

An electrode of the type described above has been employed by physicians obtaining electrocardiograms on human patients. It was capable of holding the electrode firmly in place much longer than the one-half of an hour normally used to perform an electrocardiogram. The disclosed suction cup worked so well that it needed to be removed to prevent the breaking of surface blood vessels.

Obviously, many modifications and variations of the present invention are possible in the light of the above teachings, and, it is therefore understood that the invention may be practiced otherwise than as specifically described.

What is claimed is:

1. An apparatus located on the body of a living animal for sensing electrical potentials therein comprising:
    means having an outwardly reaching member for electrically coupling the electrical potentials to remote circuitry, the electrically coupling means further includes a ring shaped member coupled to the outwardly reaching member and
    means coupled to the outwardly reaching member for holding the electrically coupling means firmly against the animal's body, the holding means having a lip portion for sealingly engaging the animal's body, an annular shoulder portion for forcing the outwardly reaching portion toward the animal's body to ensure the firm holding of the electrically coupling means thereon, a frustoconically shaped shell portion interconnecting the lip portion and the annular shoulder portion and a cup shaped shell portion mounted on the annular shoulder portion to define a continuously extending chamber, the ring shaped member is carried on the outside of the holding means where the lip portion is joined to the frustoconically shaped shell portion to ensure the firm holding of the electrically coupling means irrespective of its radial orientation from the holding means.

2. An apparatus according to claim 1 in which the lip portion, frustoconically shaped shell portion and cup shaped shell portion are integrally formed from a resilient compound to urge the continuously extending chamber to an extended configuration thereby creating a vacuum to further ensure the firm holding of the electrically coupling means.

3. An apparatus according to claim 2 in which the lip portion, frustoconically shaped shell portion, and cup shaped portion allow a one-handed deformation thereof, thereby reducing the chamber's volume and creating the vacuum after being held on the animal's body.

* * * * *